US012285290B2

(12) United States Patent
Teraishi et al.

(10) Patent No.: US 12,285,290 B2
(45) Date of Patent: Apr. 29, 2025

(54) MOUNTING MEMBER AND MEDICAL APPARATUS

(71) Applicant: NIHON KOHDEN CORPORATION, Tokyo (JP)

(72) Inventors: Masaki Teraishi, Tokorozawa (JP); Takamitsu Shimizu, Tokorozawa (JP); Takanori Sato, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 140 days.

(21) Appl. No.: 16/860,163

(22) Filed: Apr. 28, 2020

(65) Prior Publication Data

US 2020/0367857 A1 Nov. 26, 2020

(30) Foreign Application Priority Data

May 24, 2019 (JP) .................................. 2019-098087

(51) Int. Cl.
*A61B 8/00* (2006.01)
(52) U.S. Cl.
CPC .......... *A61B 8/4433* (2013.01); *A61B 8/4405* (2013.01); *A61B 8/461* (2013.01)
(58) Field of Classification Search
CPC ....... A61B 8/4405; A61B 8/4433; A61B 8/00; A61B 8/4209; H02G 3/32; H01B 7/0045; F16B 2/22
See application file for complete search history.

(56) References Cited

U.S. PATENT DOCUMENTS

| 4,609,171 A * | 9/1986 | Matsui | H02G 3/32 |
| | | | 248/316.1 |
| 5,673,696 A * | 10/1997 | Bidwell | G10K 11/004 |
| | | | 600/437 |
| 6,629,927 B1 * | 10/2003 | Mesaros | A61B 50/13 |
| | | | 600/437 |
| 6,821,250 B2 * | 11/2004 | Mesaros | A61B 8/00 |
| | | | 600/437 |

(Continued)

FOREIGN PATENT DOCUMENTS

| EP | 2 243 430 A1 | 10/2010 |
| JP | 2004-053588 A | 2/2004 |

(Continued)

OTHER PUBLICATIONS

European Search Report issued in European Patent Application No. EP 20 17 2232.9 dated Oct. 5, 2020.

(Continued)

*Primary Examiner* — Angela M Hoffa
*Assistant Examiner* — Younhee Choi
(74) *Attorney, Agent, or Firm* — MCDONALD HOPKINS LLC (57) ABSTRACT

A mounting member which is to be attached to a cart to which a monitor configured to display an ultrasonic image is fixed, the mounting member on which an ultrasonic measurement apparatus configured to acquire the ultrasonic image is to be mounted, the mounting member includes a fixing portion to which at least a part of a cable and connector part that are connected to a probe of the ultrasonic measurement apparatus is to be fitted and fixed.

6 Claims, 6 Drawing Sheets

(56) References Cited

U.S. PATENT DOCUMENTS

| | | | |
|---|---|---|---|
| 8,128,050 B1* | 3/2012 | Sliger | A61B 8/4433 |
| | | | 248/51 |
| 9,866,004 B2* | 1/2018 | Vaccaro | H02G 3/32 |
| 9,877,699 B2 | 1/2018 | Chiang et al. | |
| 11,202,616 B2* | 12/2021 | Wood | A61B 8/00 |
| 2003/0236463 A1 | 12/2003 | Mesaros et al. | |
| 2007/0205785 A1* | 9/2007 | Nilsson | A61B 8/4218 |
| | | | 600/459 |
| 2008/0146922 A1* | 6/2008 | Steins | A61B 8/546 |
| | | | 600/437 |
| 2011/0186696 A1* | 8/2011 | Hsieh | F16L 3/12 |
| | | | 248/74.1 |
| 2014/0088420 A1* | 3/2014 | Lindahl | A61B 8/4422 |
| | | | 600/437 |
| 2014/0117635 A1 | 5/2014 | Ninomiya et al. | |
| 2015/0181629 A1 | 6/2015 | Jun | |
| 2015/0219132 A1* | 8/2015 | Lacroix | F16L 55/035 |
| | | | 24/455 |
| 2015/0320298 A1 | 11/2015 | Missov et al. | |
| 2017/0122463 A1* | 5/2017 | Vaccaro | F16L 3/1075 |
| 2018/0168548 A1 | 6/2018 | Chiang et al. | |
| 2019/0125064 A1* | 5/2019 | de Jonge | A61B 8/4209 |
| 2019/0223834 A1* | 7/2019 | Nukaya | A61B 8/4209 |
| 2019/0269383 A1* | 9/2019 | Wood | A61B 8/4405 |
| 2019/0380681 A1* | 12/2019 | Meurer | A61B 8/4427 |
| 2020/0060647 A1* | 2/2020 | Ruff | A61B 8/4209 |
| 2020/0315573 A1* | 10/2020 | Kang | A61B 8/40 |
| 2022/0037869 A1* | 2/2022 | Knobloch | H02G 3/32 |
| 2022/0378398 A1* | 12/2022 | Eda | A61B 8/4209 |

FOREIGN PATENT DOCUMENTS

| | | | | |
|---|---|---|---|---|
| JP | 2011244996 A | * | 12/2011 | |
| JP | 2013172778 A | * | 9/2013 | A61B 8/4405 |
| KR | 20190102598 | * | 9/2019 | A61B 8/4209 |
| WO | 2014-207593 A1 | | 12/2014 | |
| WO | 2018-083519 A1 | | 5/2018 | |
| WO | WO-2019093607 A1 | * | 5/2019 | A61B 8/4427 |

OTHER PUBLICATIONS

Japanese Office Action issued Jan. 31, 2023 issued in JP Patent Application No. 2019-098087.

* cited by examiner

MOUNTING MEMBER AND MEDICAL APPARATUS

CROSS-REFERENCE TO RELATED APPLICATIONS

This application is based upon and claims the benefit of priority from prior Japanese patent application No. 2019-098087, filed on May 24, 2019, the entire contents of which are incorporated herein by reference.

TECHNICAL FIELD

The presently disclosed subject matter relates to a mounting member and a medical apparatus.

BACKGROUND ART

Various vital signs (such as the blood pressure, the body temperature, the respiration, the pulse rate, and the arterial oxygen saturation) are widely used as information for knowing the condition of a subject.

Recently, a technique has been proposed for simultaneously performing measurements of vital signs, and ultrasonic diagnosis using an ultrasonic measurement apparatus such as disclosed in U.S. Patent Publication No. 2018/0168548. In an emergency medical site, particularly, the condition in the body of the patient is first checked by using an ultrasonic measurement apparatus.

In the case where measurements of vital signs, and ultrasonic diagnosis are to be simultaneously performed, as described above, an ultrasonic measurement apparatus is combined with a related-art medical apparatus for acquiring vital signs. When a cable connected to a probe of the ultrasonic measurement apparatus is randomly placed, therefore, the workability of the user is poor. Consequently, it is requested to develop a mounting member on which an ultrasonic measurement apparatus is to be mounted, and which prevents a cable connected to a probe from being randomly placed.

The invention has been conducted in order to solve the problem. It is an object of the presently disclosed subject matter to provide a mounting member and medical apparatus in which, in the case where measurements of vital signs, and ultrasonic diagnosis are to be simultaneously performed, the workability of the user can be improved.

SUMMARY OF INVENTION

According to an aspect of the presently disclosed subject matter, there is provided a mounting member which is to be attached to a cart to which a monitor configured to display an ultrasonic image is fixed, the mounting member on which an ultrasonic measurement apparatus configured to acquire the ultrasonic image is to be mounted, the mounting member comprising: a fixing portion to which at least a part of a cable and connector part that are connected to a probe of the ultrasonic measurement apparatus is to be fitted and fixed.

According to an aspect of the presently disclosed subject matter, there is also provided a mounting member which is to be attached to a cart to which a monitor configured to display an ultrasonic image is fixed, the mounting member on which an ultrasonic measurement apparatus configured to acquire the ultrasonic image is to be mounted, the mounting member comprising: a first mounting portion on which a probe of the ultrasonic measurement apparatus is to be mounted along a vertical direction.

According to another aspect of the presently disclosed subject matter, there is provided a medical apparatus comprising: the above mounting member; the cart; the monitor; and the ultrasonic measurement apparatus.

DESCRIPTION OF EMBODIMENTS

An embodiment of the presently disclosed subject matter will be described with reference to the drawings. In the description of the drawings, identical components are denoted by the same reference numerals, and duplicated description is omitted. In the drawings, the dimension ratios are exaggerated for the sake of convenience in description, and may be sometimes different from the actual ratios.

Figure 1:
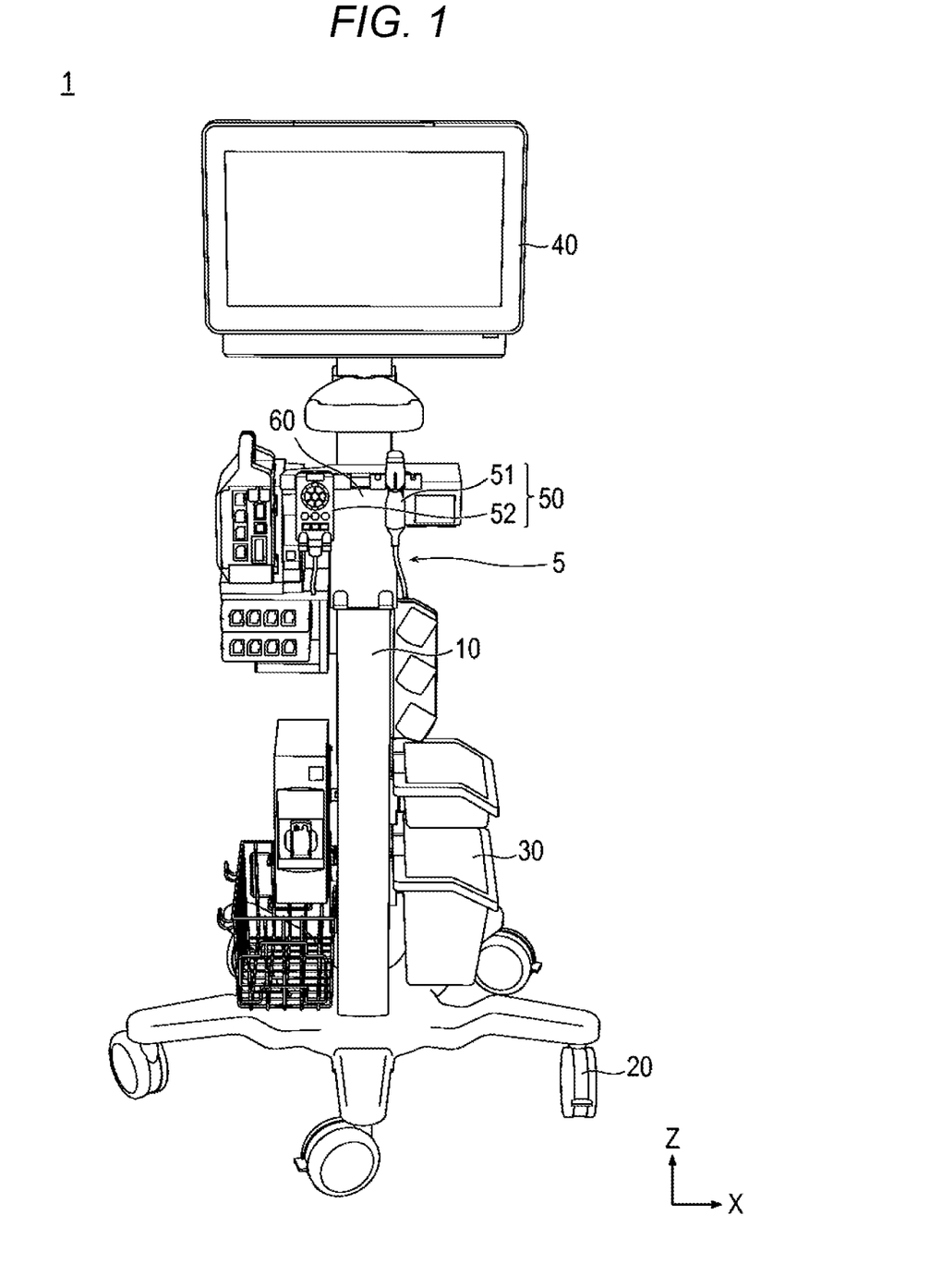
FIG. 1 is a view schematically illustrating a medical apparatus of an embodiment.
Figure 2:
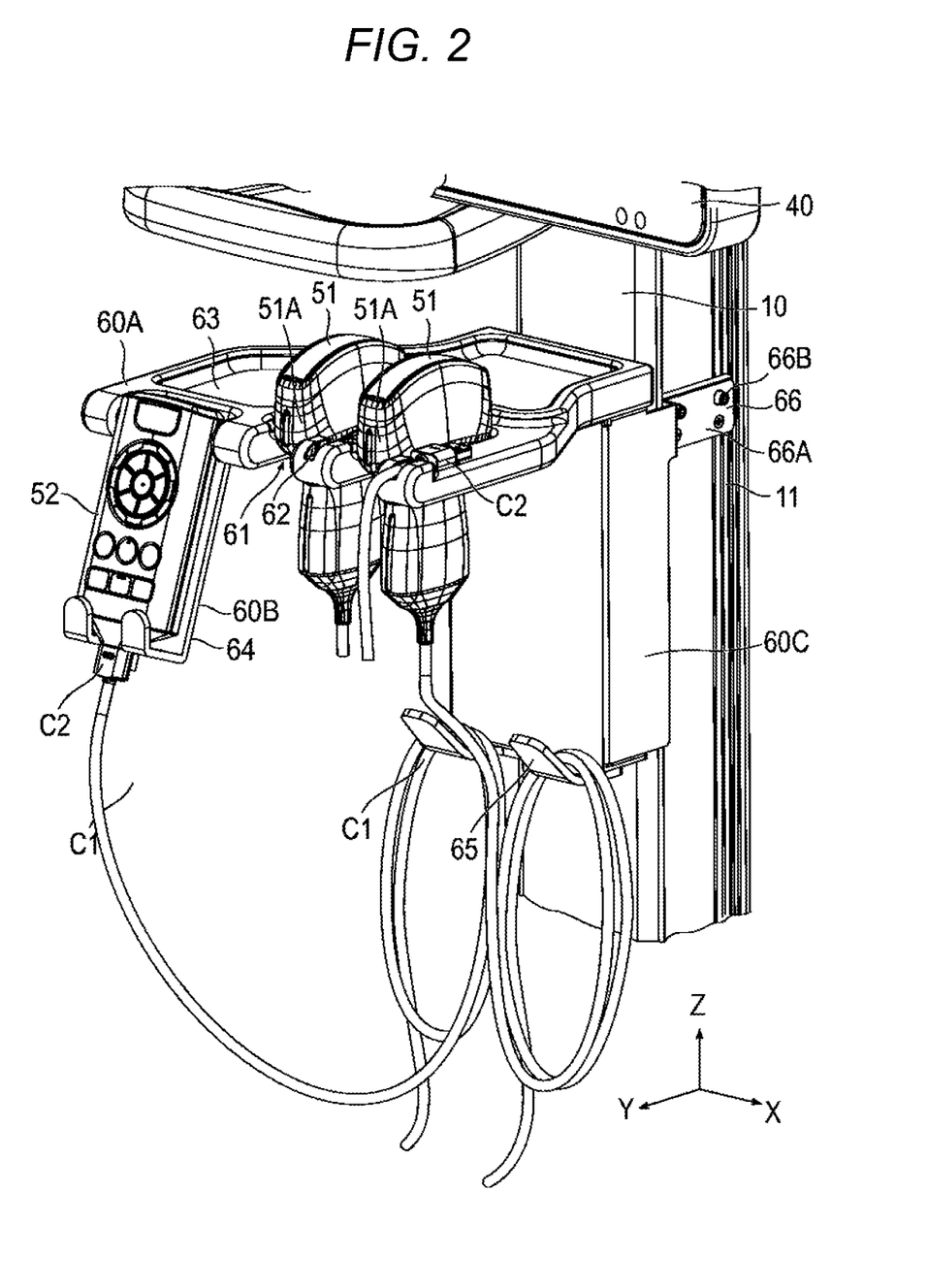
FIG. 2 is a perspective view illustrating a manner in which an ultrasonic measurement apparatus is mounted on a mounting member of the embodiment.
Figure 3:
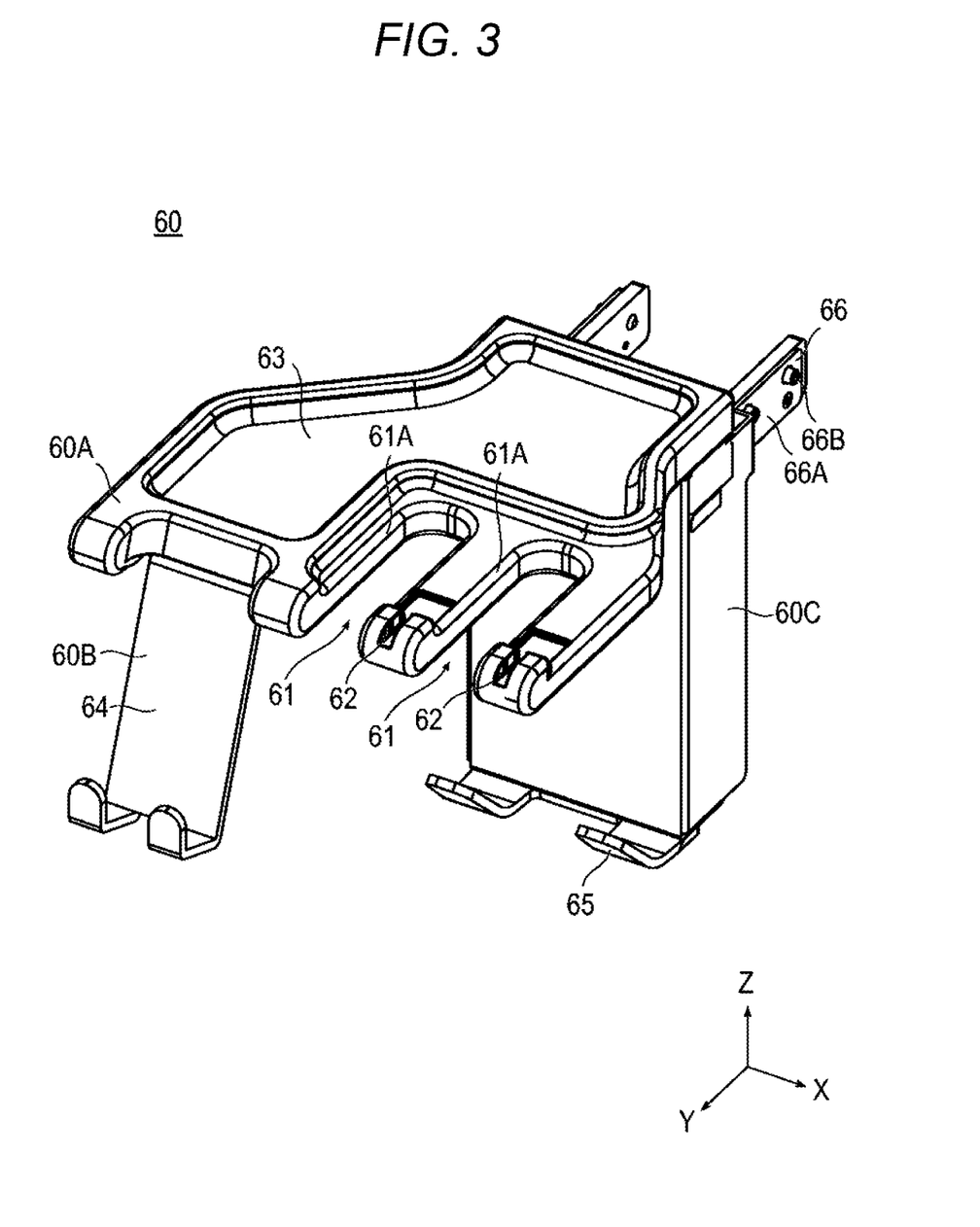
FIG. 3 is a perspective view illustrating the mounting member of the embodiment.
Figure 4:
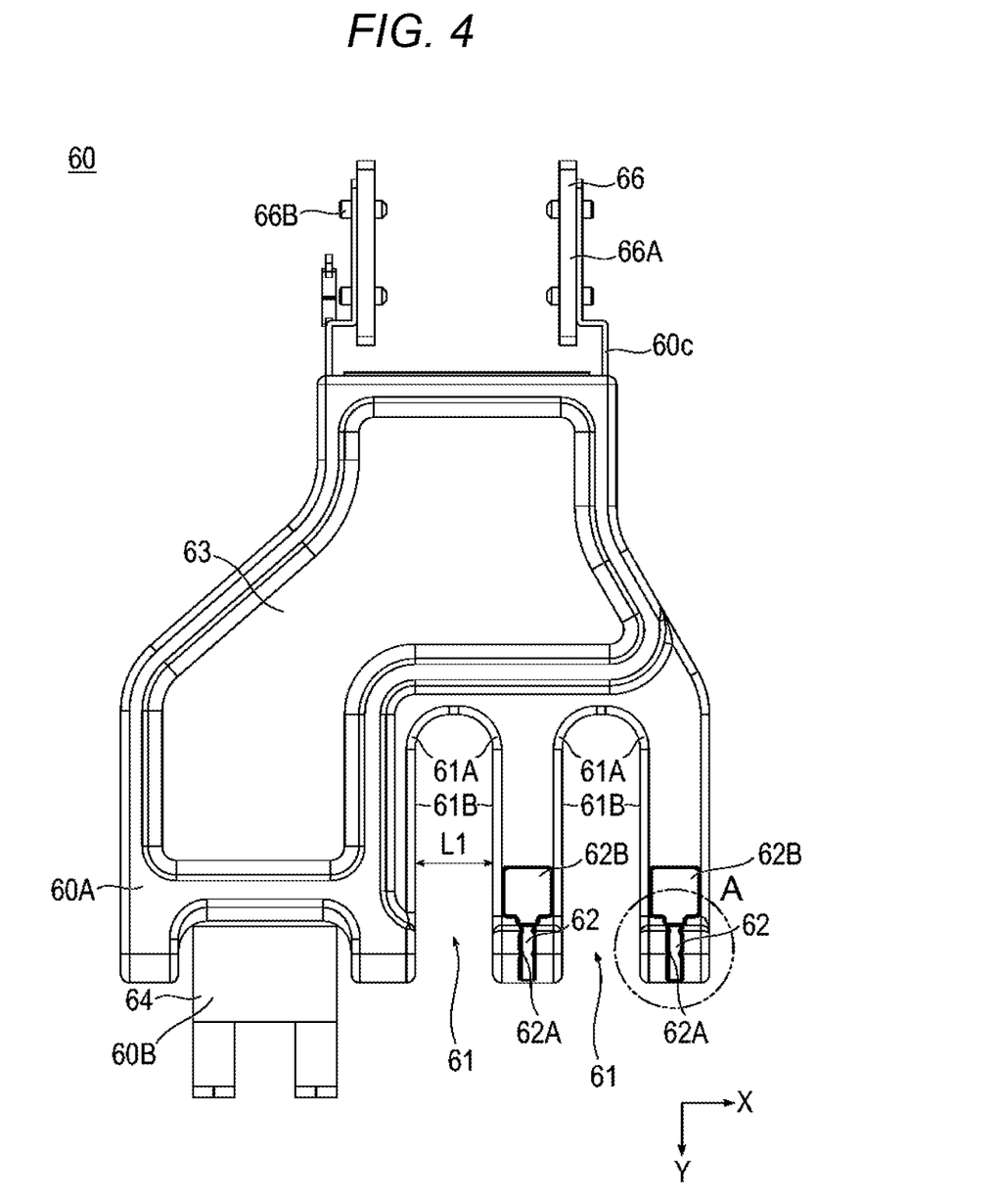
FIG. 4 is a plan view illustrating the mounting member of the embodiment.
Figure 5:
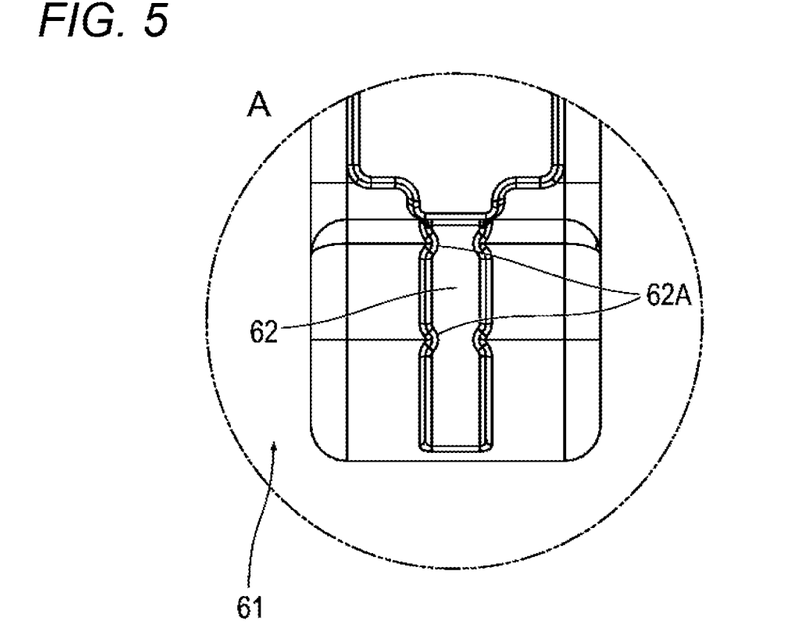
FIG. 5 is an enlarged view of the portion A in FIG. 4.

FIG. 1 is a view schematically illustrating a medical apparatus 1 of the embodiment, FIG. 2 is a perspective view illustrating a manner in which an ultrasonic measurement apparatus 50 is mounted on a mounting member 60 of the embodiment, FIG. 3 is a perspective view illustrating the mounting member 60 of the embodiment, FIG. 4 is a plan view illustrating the mounting member 60 of the embodiment, and FIG. 5 is an enlarged view of the portion A in FIG. 4.

The medical apparatus 1 can simultaneously perform measurements of vital signs (such as the blood pressure, the body temperature, the respiration, the pulse rate, and the arterial oxygen saturation), and ultrasonic diagnosis. As illustrated in FIG. 1, the medical apparatus 1 may include: a post 10 that elongates in the vertical direction; casters 20 that are attached to the lower portion of the post 10; a housing section 30 that is attached to the post 10, and that houses a container of gel for ultrasonic measurement, and the like; a monitor 40 that is attached to the upper portion of the post 10; an ultrasonic measurement apparatus 50 for performing ultrasonic measurement; and a mounting member 60 on which the ultrasonic measurement apparatus 50 is mounted. The post 10, the casters 20, and the housing section 30 constitute a cart 5. The monitor 40 is fixed to the upper portion of the cart 5.

In the following description, the side in which the screen of the monitor 40 exists is referred to as the front side, and that in which the lateral surface of the monitor 40 exists is referred to as the lateral side.

As illustrated in FIG. 1, the post 10 is disposed so as to elongate in the vertical direction. As illustrated in FIG. 2, a groove portion 11 that elongates in the vertical direction is disposed in the lateral surface of the post 10. An attachment portion 66 that is disposed in the mounting member 60 which will be described later is attached so as to be slidable in the vertical direction.

As illustrated in FIG. 1, five casters 20 are attached to the lower portion of the post 10. Since the casters 20 are attached in this way, the medical apparatus 1 can freely move on the floor.

As illustrated in FIG. 1, the monitor 40 is attached to the upper portion of the cart 5. Various vital signs that are measured based on vital signs signals which are acquired from various sensors connected to a subject are displayed on the monitor 40. Furthermore, an ultrasonic image that is acquired by the ultrasonic measurement apparatus 50 is displayed on the monitor 40.

When a probe 51 is contacted with the body of the subject, the ultrasonic measurement apparatus 50 acquires an ultrasonic image of the interior of the body of the subject. As illustrated in FIG. 2, the ultrasonic measurement apparatus 50 may include the probe 51 that is to be contacted with the body of the subject, and a remote controller 52 to which a connector part C2 that is disposed in one end of a cable C1 connected to the probe 51 is connected. The cable C1 connected to the probe 51 is, for example, a USB cable, and the remote controller 52 is USB-connected to the USB cable.

The probe 51 may include: a transmitter (not shown) that is to be contacted with the body of the subject, and that transmits an ultrasonic wave; a receiver (not shown) that receives the ultrasonic wave which is reflected from the body of the subject; and a controller (not shown) to which a received ultrasonic wave signal is transmitted, and which acquires an ultrasonic image. The probe 51 may be any of the convex type, the sector type, and the linear type.

As illustrated in FIG. 2, the probe 51 may include an expanded portion 51A that is in the vicinity of the middle in the Z direction, and that extends in the X and Y directions. Since the expanded portion 51A is disposed in the probe 51 in this manner, the user can preferably grasp the probe 51. In the embodiment, two probes 51 are disposed. The cable C1 that is connected to the probe 51 is wound around a hooking portion 65 of the mounting member 60 that will be described later, to be hooked thereon. Another connector part C2 that is disposed in the other end of the cable C1 is connected to the remote controller 52.

Various operations can be remotely controlled through the remote controller 52. For example, the remote controller 52 can perform activation and the like of the transmitter, receiver, and controller of the probe 51. A camera is incorporated in the remote controller 52, and can take an image of a situation of the scene.

The ultrasonic image that is acquired by the ultrasonic measurement apparatus 50 is displayed on the monitor 40.

With reference to FIGS. 2 to 5, next, the configuration of the mounting member 60 will be described in detail. In order to facilitate the description, the lateral direction in FIG. 4 is referred to as the X direction, the vertical direction in FIG. 4 is referred to as the Y direction, and the direction perpendicular to the sheet is referred to as the Z direction.

As illustrated in FIG. 2, the ultrasonic measurement apparatus 50 is mounted on the mounting member 60. The mounting member 60 is detachably attached to the cart 5.

As illustrated in FIGS. 2 to 4, the mounting member 60 may include; a planar portion 60A that is planarly configured along the XY plane; a first extended portion 60B that is extended from the left side of the planar portion 60A in the X direction, and the front side in the Y direction, and downward in the Z direction, and toward the front side in the Y direction; and a second extended portion 60C that is extended from the rear side of the planar portion 60A in the Y direction, and downward in the Z direction.

The planar portion 60A and the first extended portion 60B are fixed to each other. The method of fixing together the planar portion 60A and the first extended portion 60B is not particularly limited. The planar portion 60A and the second extended portion 60C are fixed to each other. The method of fixing together the planar portion 60A and the second extended portion 60C is not particularly limited.

As illustrated in FIGS. 3 and 4, the planar portion 60A is disposed in the XY plane. Although the material of the planar portion 60A is not particularly limited, the portion is configured by, for example, a resin. As illustrated in FIGS. 2 and 3, first mounting portions 61 on which the probes 51 are respectively mounted, fixing portions 62 to which the cables C1 connected to the probes 51 are respectively fixed, and a placing portion 63 on which small articles are to be placed are disposed in the planar portion 60A.

As illustrated in FIGS. 3 and 4, the first mounting portions 61 have a shape that is recessed in a U-like manner toward the rear side in the Y direction. As illustrated in FIGS. 3 and 4, two first mounting portions 61 are juxtaposed in the X direction so that the two probes 51 are mounted on the portions, respectively. Hereinafter, only one of the two first mounting portions 61 will be described in order to facilitate the description of the configurations of the first mounting portions 61. The description of the one first mounting portion 61 is applicable also to the other first mounting portion 61.

The first mounting portion 61 is configured so that the length L1 (see FIG. 4) of the portion in the X direction is shorter than the X-direction length of the expanded portion 51A of each of the probes 51. The length L1 of the first mounting portion 61 in the X direction is longer than the X-direction length of the probe 51 excluding the expanded portion 51A. A tapered portion 61A is formed in the upper surface of the first mounting portion 61 so that the probe 51 is prevented from slipping off, and can be mounted from the upper side. In the first mounting portion 61, the long sides 61B that constitute the portion, and that are opposed to each other are approximately parallel to each other. On the thus configured first mounting portion 61, the probe 51 can be mounted so that the longitudinal direction of the probe 51 (the longitudinal direction as viewed from the upper side in FIG. 2) is oriented in the Y direction. Since the first mounting portion 61 is disposed as described above, the user can easily pick up the probe 51, and can quickly perform the inspection.

As illustrated in FIGS. 3 and 4, the fixing portion 62 is disposed on the right side of the first mounting portion 61 in the X direction. The position where the fixing portion 62 is disposed is not limited to the above-described position.

In the embodiment, the cable Cl connected to the probe 51 is fixed by being fitted into the fixing portion 62. As illustrated in FIGS. 4 and 5, the fixing portion 62 may include constricted parts 62A each of which is configured so that its width is smaller than the width of the outer circumference of the cable C1 that is coated with a resin material, and a housing part 62B which is disposed on the rear side of the constricted parts 62A in the Y direction, and in which the connector part C2 connected to the cable C1 is housed and fixed. Although the housing part 62B has a structure that substantially corresponds to a USB cable, the structure is not necessarily limited to this. The housing part may have a structure that is configured considering the shape of another connector.

Because of the elastic force of the resin material, therefore, the cable C1 is fixed to the constricted parts 62A of the fixing portion 62, and the connector part C2 is fixed to the housing part 62B of the fixing portion 62. In the case where the planar portion 60A is made of a resin, the cable C1 is fixed to the constricted parts 62A of the fixing portion 62, also by the elastic force of the constricted parts 62A of the fixing portion 62. Although it is preferred that both the cable C1 and the connector part C2 are fixed as described above, only a part of the cable C1 may be fixed by using the constricted parts 62A. As illustrated in FIG. 5, two constricted parts 62A are disposed in the fixing portion 62 along the Y direction. Since the two constricted parts 62A of the fixing portion 62 are disposed in the Y direction as described above, the cable C1 can be fixed at two places. Therefore, the cable C1 can be adequately prevented from slipping off. The disposition of the two constricted parts 62A in the fixing portion 62 along the Y direction allows the user to select one of the two constricted parts 62A, and fix the cable C1 by using the selected constricted part.

Small articles are to be placed on the placing portion 63. The placing portion 63 is disposed in the rear side of the first mounting portion 61 in the Y direction and in the left side of the first mounting portion in the X direction. The small articles that are to be placed on the placing portion 63 are not particularly limited, and an example of the small articles is a container of gel for ultrasonic measurement.

A second mounting portion 64 on which the remote controller 52 of the ultrasonic measurement apparatus 50 is to be mounted is configured in the first extended portion 60B. The first extended portion 60B is configured by covering the circumference of a metal plate with a resin.

The second mounting portion 64 is disposed on the left side of the first mounting portion 61 in the X direction. The tip end of the second mounting portion 64 has a U-like shape as viewed from the lateral side. According to the thus configured second mounting portion 64, the remote controller 52 can be placed so that the operating surface of the remote controller is directed to the front side. Even when the user stands on either of the right and left sides of the medical apparatus 1, therefore, the user can view the operating surface of the remote controller 52, and therefore the operability of the user can be improved.

The second extended portion 60C is configured by painting the circumference of a metal plate with a coating composition. The hooking portion 65 on which the cable C1 connected to the probe 51 is to be hooked, and the attachment portion 66 which is attached to the post 10 is attached are disposed in the second extended portion 60C.

As illustrated in FIG. 2, the cable C1 is hooked on the hooking portion 65 while being wound therearound. The hooking portion 65 is disposed in the lower part of the second extended portion 60C in the Z direction. The hooking portion 65 has a U-like shape as viewed from the lateral side. Since the hooking portion 65 is disposed in the mounting member 60 as described above, it is possible to prevent the cable C1 from being randomly placed. The hooking portion 65 is configured by covering the circumference of a metal plate with a resin.

As illustrated in FIGS. 2 to 4, the attachment portion 66 is disposed in the rear side of the second extended portion 60C in the Y direction. The attachment portion 66 may include a pair of body parts 66A that extend toward the rear side in the Y direction, and fastening members 66B that are placed so as to be screwable into threaded holes (not shown) which are disposed in the body parts 66A.

The pair of body parts 66A are disposed along the X direction. As illustrated in FIG. 2, the pair of body parts 66A are separated from each other by a distance that is larger than the width of the post 10 in the X direction.

Two fastening members 66B are disposed along the Y direction for each of the body parts 66A. The pair of body parts 66A are positioned in the Z direction under a state where the fastening members 66B are loosened so that the pair of body parts 66A can be slid in the Z direction, and thereafter the pair of fastening members 66B are fastened so as to approach to each other. This causes the fastening members 66B to be fixed to the post 10, thereby fixing the mounting member 60 to the post 10.

The presently disclosed subject matter is not limited to the embodiment, and the configuration may be variously modified within the scope of the accompanying claims.

In the above-described embodiment, for example, the mounting member 60 is detachably attached to the cart 5. However, the mounting member 60 may be non-detachably attached to the cart 5.

In the above-described embodiment, moreover, the two constricted parts 62A are disposed along the longitudinal direction of the cable C1. However, one or three or more constricted parts 62A may be disposed.

In the above-described embodiment, moreover, the two first mounting portions 61 are disposed. However, one or three or more first mounting portions 61 may be disposed.

In the above-described embodiment, moreover, the first mounting portions 61 have a shape that is recessed in a U-like manner toward the rear side in the Y direction. However, the first mounting portions 61 may have a rectangular shape or the like that is chamfered.

Figure 6:
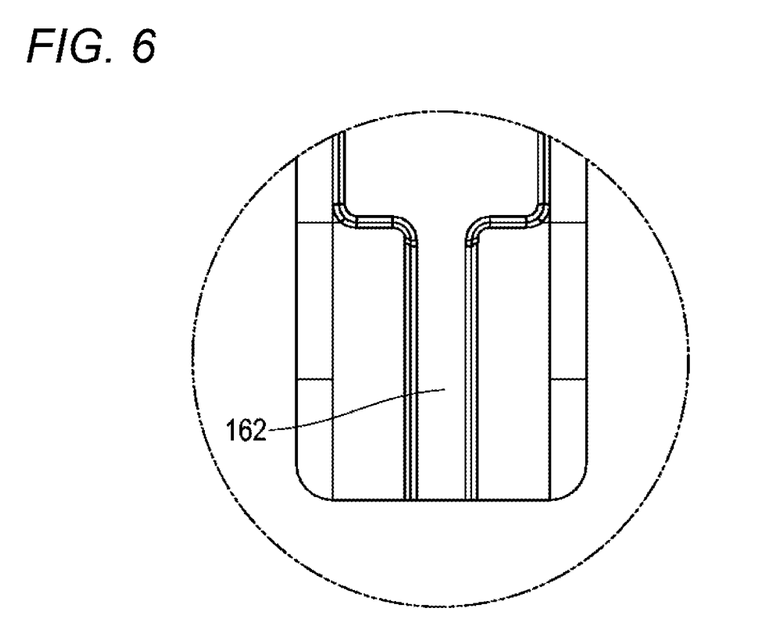
FIG. 6 illustrates a fixing portion in Modification 1, and corresponds to FIG. 5.

In the above-described embodiment, as illustrated in FIG. 5, the fixing portion 62 has the constricted parts 62A. As illustrated in FIG. 6, however, a fixing portion 162 may have a configuration where constricted parts are not formed. In this case, the fixing portion 162 is configured so that its width is smaller than the width of the outer circumference of the cable C1 that is coated with a resin material. According to the configuration, the cable C1 is fixed to the fixing portion 162 by the elastic force of the resin material.

Figure 7:
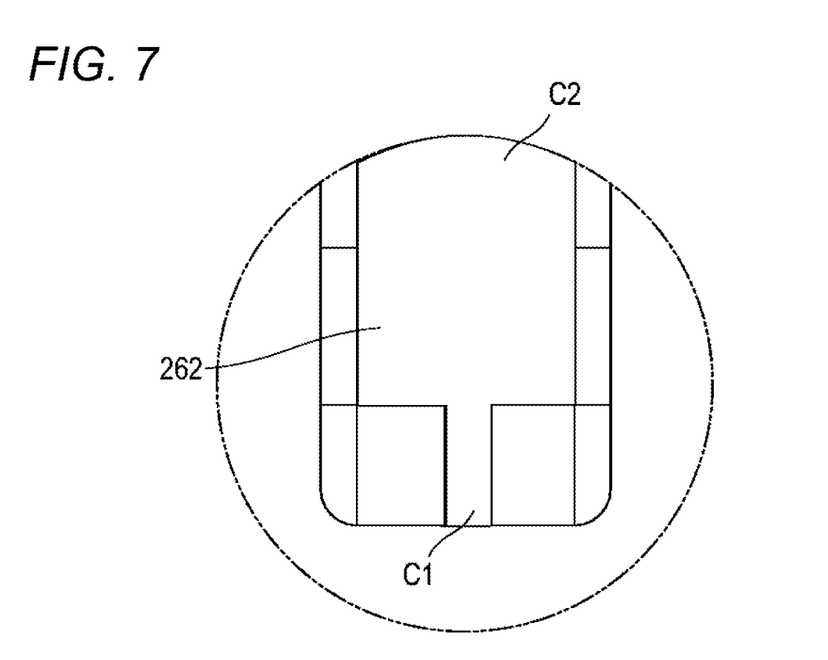
FIG. 7 illustrates a fixing portion in Modification 2, and corresponds to FIG. 5.

In the above-described embodiment, moreover, the housing part 62B is configured so that the width in the X direction is larger than the width of the connector part C2. As illustrated in FIG. 7, however, a fixing portion 262 may have a configuration where the cable C1 is not fixed to the fixing portion, but the connector part C2 is fitted into the fixing portion to be fixed thereto. In the modification, the fixing portion 262 is configured by a groove having a substantially rectangular shape in a plan view that corresponds in width to the connector part C2. In FIG. 7, the cable C1 and the connector part C2 are illustrated in order to facilitate understanding of the configuration.

Figure 8:
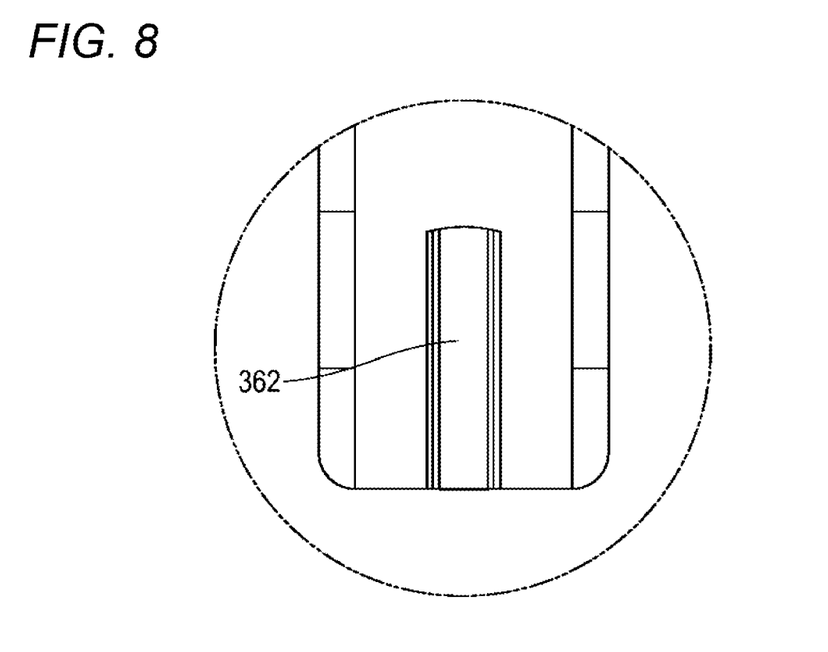
FIG. 8 illustrates a fixing portion in Modification 3, and corresponds to FIG. 5.

In the above-described embodiment, as illustrated in FIG. 4, the housing part 62B in which the connector part C2 connected to the cable C1 is to be housed is disposed on the rear side of the fixing portion 62 in the Y direction. As illustrated in FIG. 8, however, the housing part 62B in which the connector part C2 is to be housed may not be disposed in a fixing portion 362.

The fixing portion in the presently disclosed subject matter is not limited to have the above-described configurations, as far as the fixing portion is configured so that at least a part of the cable C1, at least a part of the connector part C2, or at least a part of the cable C1 and at least a part of the connector part C2 are fitted and fixed to the fixing portion.

In the above-described embodiment, the connector part C2 is fixed to the housing part 62B. However, a configuration where the connector part C2 is not fixed to the housing part 62B, but simply housed therein may be employed.

According to the mounting member and medical apparatus that are described above, the fixing portion is disposed into which at least a part of the cable and connector part that are connected to the probe is fitted to be fixed thereto. Therefore, it is possible to prevent the cable connected to the probe from being randomly placed. In the case where measurements of vital signs, and ultrasonic diagnosis are to be simultaneously performed, consequently, the workability of the user can be improved.

According to the mounting member and medical apparatus that are described above, the first mounting portion is disposed on which a probe of the ultrasonic measurement apparatus is to be mounted along a vertical direction. Therefore, it is possible for the user to easily pick up the probe, and quickly perform the inspection. In the case where measurements of vital signs, and ultrasonic diagnosis are to be simultaneously performed, consequently, the workability of the user can be improved.

What is claimed is:

1. A mounting member which is to be attached to a cart to which a monitor configured to display an ultrasonic image is fixed, the mounting member on which an ultrasonic measurement apparatus configured to acquire the ultrasonic image is to be mounted, the mounting member comprising:
    a planar portion that is planar member extending along a horizontal direction, the planar portion comprising:
        an extended portion located at a first end of the planar portion along the horizontal direction and comprising an attachment portion configured to attach to the cart;
        a fixing portion to which at least a part of a cable and/or at least a part of a connector part that are connected to a probe of the ultrasonic measurement apparatus is to be fitted and fixed; and
        a first mounting portion on which the probe is to be mounted along a vertical direction and located at a second end of the planar portion along the horizontal direction, the second end being opposite the first end in the horizontal direction,
    wherein the cable has two ends, a first end being connected to the probe and a second end being connected to the connector part,
    wherein both the at least part of the cable and the at least part of the connector part are fitted and fixed to the fixing portion,
    wherein the fixing portion has a first constricted part including a first pair of protrusions, the first pair of protrusions extending towards one another in a transverse direction of the cable, the first pair of protrusions being in contact with the cable to fix the cable,
    wherein a gap between the first pair of protrusions is narrower than a diameter of the cable,
    wherein the fixing portion is a groove formed in a straight line along a longitudinal direction of the cable, and
    wherein a second constricted part having a second pair of protrusions disposed along the longitudinal direction of the cable and into which the cable is to be fitted is provided together with the first constricted part at different positions in the groove,
    wherein the first mounting portion includes a recess in the form of a U-shape, and
    wherein a tapered portion is formed in the recess in an upper surface side of the first mounting portion, such that the probe is mountable from an upper side of the first mounting portion and is prevented from slipping off the first mounting portion.

2. The mounting member according to claim 1, wherein long sides that constitute the first mounting portion, and that are opposed to each other are approximately parallel to each other.

3. The mounting member according to claim 1, further comprising:
    a second mounting portion on which a remote controller of the ultrasonic measurement apparatus is to be mounted so that an operating surface of the remote controller is directed toward a screen of the monitor.

4. A medical apparatus comprising:
    the mounting member according to claim 1;
    the cart;
    the monitor; and
    the ultrasonic measurement apparatus.

5. The mounting member according to claim 1,
    wherein the fixing portion includes two surfaces at the first constricted part which are opposed to each other so that the cable is sandwiched between the two surfaces, and
    wherein a space between the two surfaces at the first constricted part is narrower than another space.

6. The mounting member according to claim 1, wherein an elastic force of the first and second pairs of protrusions fixes the cable.

* * * * *